(12) United States Patent
Ma

(10) Patent No.: US 8,859,006 B2
(45) Date of Patent: Oct. 14, 2014

(54) SEMEN CASSIAE SOFT CAPSULE FOR REDUCING FAT AND LOSING WEIGHT AND PREPARATION METHOD THEREOF

(76) Inventor: Jianzhong Ma, Chengdu (CN)

( * ) Notice: Subject to any disclaimer, the term of this patent is extended or adjusted under 35 U.S.C. 154(b) by 38 days.

(21) Appl. No.: 13/806,109

(22) PCT Filed: Jun. 28, 2011

(86) PCT No.: PCT/CN2011/076453
§ 371 (c)(1),
(2), (4) Date: Dec. 20, 2012

(87) PCT Pub. No.: WO2012/003768
PCT Pub. Date: Jan. 12, 2012

(65) Prior Publication Data
US 2013/0099403 A1 Apr. 25, 2013

(30) Foreign Application Priority Data
Jul. 5, 2010 (CN) .......................... 2010 1 0216675

(51) Int. Cl.
| | |
|---|---|
| A61K 35/64 | (2006.01) |
| A61K 36/484 | (2006.01) |
| A61K 36/18 | (2006.01) |
| A61K 9/48 | (2006.01) |
| A61K 36/61 | (2006.01) |
| A61K 36/482 | (2006.01) |
| A61K 36/185 | (2006.01) |
| A61K 9/20 | (2006.01) |

(52) U.S. Cl.
CPC .............. *A61K 9/4833* (2013.01); *A61K 36/61* (2013.01); *A61K 9/4875* (2013.01); *A61K 36/482* (2013.01); *A61K 9/2095* (2013.01); *A61K 9/2086* (2013.01); *A61K 36/185* (2013.01); *A61K 36/484* (2013.01)
USPC ............ 424/539; 424/757; 424/773; 424/776

(58) Field of Classification Search
None
See application file for complete search history.

(56) References Cited

U.S. PATENT DOCUMENTS

| | | | | |
|---|---|---|---|---|
| 2004/0161524 | A1* | 8/2004 | Sakai et al. ................... | 426/655 |
| 2008/0279902 | A1* | 11/2008 | Luria et al. ................... | 424/401 |
| 2010/0028318 | A1* | 2/2010 | Saito et al. ................... | 424/94.1 |

FOREIGN PATENT DOCUMENTS

| | | | |
|---|---|---|---|
| CN | 1082364 | | 4/2002 |
| CN | 101284122 A | * | 10/2008 |
| CN | 101524441 | | 9/2009 |
| CN | 101595927 | | 12/2009 |
| CN | 101698028 | | 4/2010 |
| CN | 101810336 A | * | 8/2010 |
| CN | 101862367 | | 10/2010 |
| CN | 102228242 A | * | 11/2011 |

OTHER PUBLICATIONS

Chen et al., "The Research Progress of Chinese Traditional Medicine with Effect of Losing Weight", Journal of Shaanxi College of Traditional Chinese Medicine, vol. 26, No. 6, pp. 62-64, Nov. 2003. English abstract attached.

Guo et al., "The Research Progress of Losing Weight by Chinese Traditional Medicine", Journal of Chinese Medicinal Materials, vol. 25, No. 7, pp. 534-537, Jul. 2002. English abstract attached.

International Search Report in the parent PCT application No. PCT/CN2011/076453, dated Sep. 15, 2011.

\* cited by examiner

*Primary Examiner* — Chris R Tate
(74) *Attorney, Agent, or Firm* — Chen Yoshimura LLP

(57) ABSTRACT

A *Semen Cassiae* soft capsule for lowering blood lipids and losing weight and the preparation method thereof. The content of the soft capsule consist of the following components by weight part: 10-60 parts of ethanol soluble extract powder of *Semen Cassiae*, 2-10 parts of aqueous soluble extract powder of *Radix Glycyrrhizae*, 10-30 parts of evening primrose oil, 5-20 parts of sea buckthorn seed oil and 2-10 parts of beeswax. The preparation method includes the following steps: preparing all the components respectively; dissolving the ethanol soluble extract powder of *Semen Cassiae* in ethanol, adding 50% of the total weight of beeswax, heating in a water bath at 75 degrees Celsius to obtain a liquid mixture of *Semen Cassiae* and beeswax; heating the remainder beeswax with evening primrose oil, adding the liquid mixture of *Semen Cassiae* and beeswax while continuously stirring, adding aqueous soluble extract powder of *Radix Glycyrrhizae*, cooling the mixture by circulation water, adding sea buckthorn seed oil and continuously stirring to obtain the content for soft capsules, encapsulating soft capsules by conventional method to obtain the *Semen Cassiae* soft capsule.

2 Claims, No Drawings

SEMEN CASSIAE SOFT CAPSULE FOR REDUCING FAT AND LOSING WEIGHT AND PREPARATION METHOD THEREOF

BACKGROUND OF THE INVENTION

1. Field of the Invention

The present invention relates to the application of *Semen Cassiae* extract in pharmaceutical industry, especially a *Semen Cassiae* soft capsule for lowering blood lipids and losing weight and the preparation method thereof.

2. Background of the Invention

Hyperlipidemia is a common disease caused by metabolic disorders that lead to alterations in plasma lipid and lipoprotein. The clinical symptoms include elevation of total cholesterol (TC), triglyceride (TG), and low-density lipoprotein (LDL); as well as downtrend and/or decrease in high-density lipoprotein (HDL). Hyperlipidemia is known to relate to cardiovascular and cerebrovascular diseases such as coronary disease, cerebral apoplexy and high blood pressure; it is also a common cause of gallstone, pancreatitis and Alzheimer's disease. In the past decades, people's dietary structure has been shifting rapidly and dramatically. The intakes of high-calorie food such as animal fat have increased significantly. As a result, the incidence of hyperlipidemia and cardiovascular/cerebrovascular diseases has reached the highest level in human history. Meanwhile, medical evidences have shown that hyperlipidemia is often related to obesity. At present the pharmaceutical industry is working hard to develop a drug for hyperlipidemia that is with better efficacy and less side effect or adverse reaction. One of the approaches is to apply Traditional Chinese Medicine (TCM) theory together with modern pharmaceutical technology, and to develop a Traditional Chinese Medicine (TCM) preparation to lower blood lipids and lose weight. Such methods have been described in several Chinese patents, for instance, publication number CN101698028A "A Composition for lowering blood lipids and losing weight and the preparation method thereof" and publication number CN101524441 "A Composition of Traditional Chinese Medicine for lowering blood lipids and losing weight and the preparation method thereof". But these methods, especially soft capsule preparations, have a universal disadvantage that the content of capsule has low level of solid-state active ingredients, thus the efficacy is low and patients have to take a higher dosage. Meanwhile the present soft capsule manufacture technology applies mainly vegetable oil as dispersion medium, thus the concentration of aqueous and ethanol soluble drug ingredients are low in soft capsule preparations, which limit the application of soft capsule in pharmaceutical industry.

SUMMARY OF THE INVENTION

The present invention aims to provide a *Semen Cassiae* soft capsule for lowering blood lipids and losing weight with higher solid-state active ingredients content, better efficacy and the preparation method thereof.

To achieve the above-mentioned purpose, the present invention applies following techniques:

Ethanol soluble extract powder of *Semen Cassiae*: 10-60 parts
Aqueous soluble extract powder of *Radix Glycyrrhizae*: 2-10 parts
Evening primrose oil: 10-30 parts
Sea buckthorn seed oil: 5-20 parts
Beeswax: 2-10 parts The preparation method of above-mentioned ingredients include following steps:

(1) Preparation of ethanol soluble extract powder of *Semen Cassiae*: grind *Semen Cassiae* into powder, reflux extract by adding 95% ethanol 10-20 times to the weight of above-mentioned *Semen Cassiae* powder, recovery ethanol by vacuum distillation, spray drying the rest of the extract, the product is the ethanol soluble extract powder of *Semen Cassiae*.

Preparation of aqueous soluble extract powder of *Radix Glycyrrhizae*: grind *Radix Glycyrrhizae* into powder, boil extract by adding water 10-20 times to the weight of above-mentioned *Radix Glycyrrhizae* powder, condense and spray dry the extract, the product is the aqueous soluble extract powder of *Radix Glycyrrhizae*.

Preparation of evening primrose oil: commonly known as evening primroses, they are a series of flowering plants in the genus of *Oenothera*, the type genus of the family Onagraceae. Evening primrose oil is the fatty oil from evening primrose seeds. Collect ripe fruits of evening primrose in July or August, dry in the sun, crush, hull, and collect the seeds, extract oil by carbon dioxide ($CO_2$) supercritical fluid extraction.

Preparation of sea buckthorn seed oil: extract oil by carbon dioxide ($CO_2$) supercritical fluid extraction.

(2) Dissolve ethanol soluble extract powder of *Semen Cassiae* in 95% ethanol that two times to its weight, add 50% of the total weight of the beeswax, heat in a water bath at 75 degrees Celsius to obtain a liquid mixture of ethanol soluble extract powder of *Semen Cassiae*, ethanol and beeswax; co-heat the remaining 50% beeswax and the evening primrose oil until the beeswax melts, let the mixture cool down to 60 degrees Celsius, add the above-mentioned mixture of ethanol soluble extract powder of *Semen Cassiae*, ethanol and beeswax while continuously stirring; add the total amount of aqueous soluble extract powder of *Radix Glycyrrhizae*, continue stirring and cool the mixture on circulated water until the temperature is 50 degrees Celsius; add the total amount of sea buckthorn seed oil, continue stirring until the mixture is homogenous with good fluidity; encapsulate soft capsules by conventional method with temperature below 40 degrees Celsius.

In the formula of the present invention, ethanol soluble extract powder of *Semen Cassiae* is the major ingredient, which contains active components to lower blood pressure and lipids, protect liver cells and kill bacteria.

Sea buckthorn seed oil contains 103 different kinds of active components (6 vitamins, 22 fat acids, 42 lipids, 33 flavonoids and phenols). It's an essential dietary supplement for astronauts. It lowers total cholesterol (TC), triglyceride (TG) level, and raises high-density lipoprotein (HDL), thus regulates the blood lipids and prevents cardiovascular/cerebrovascular diseases.

Evening primrose oil lowers blood lipids and body weight.

The aqueous soluble extract of *Radix Glycyrrhizae* in Traditional Chinese Medicine (TCM) works as a catalyst, which enhances the effects of other ingredients in the formula.

The innovativeness and advantages of the present invention are:

(1) All ingredients in the present invention are from Traditional Chinese Medicine (TCM), which are natural and safe, thus could be administrated in long term without side effects or adverse reactions.

(2) The solid-state medicinal ingredient in the soft capsule content is much higher in the present invention; therefore the efficacy is much better.

(3) The present invention provides a novel and effective method to disperse aqueous and ethanol soluble solid-state materials in vegetable oil. (A) Beeswax melts in hot ethanol, therefore when the ethanol soluble extract powder of *Semen Cassiae* dissolves in hot beeswax and ethanol, the mixture will form a homogenous fluid with high concentration yet low viscosity. (B) The *Semen Cassiae* mixture in (A) can dissolve in the mixture of evening primrose oil and beeswax, so as the aqueous soluble extract of *Radix Glycyrrhizae*. As the ethanol vaporized from the mixture, and the temperature declined, micro particles of the ethanol soluble extract powder of *Semen Cassiae* will be separated out from the solvent and be embedded into beeswax to form a homogenous paste. This is the process of microencapsulation. Finally dilute the paste with sea buckthorn seed oil to increase fluidity for soft capsule encapsulation.

DETAILED DESCRIPTION OF THE INVENTION

Embodiment 1

Preparation of ethanol soluble extract powder of *Semen Cassiae*: grind *Semen Cassiae* into powder, reflux extract by adding 95% ethanol 10-20 times to the weight of above-mentioned *Semen Cassiae* powder, recovery ethanol by vacuum distillation, spray drying the rest of the extract, the product is the ethanol soluble extract powder of *Semen Cassiae*.

Preparation of aqueous soluble extract powder of *Radix Glycyrrhizae*: grind *Radix Glycyrrhizae* into powder, boil extract by adding water 10-20 times to the weight of above-mentioned *Radix Glycyrrhizae* powder, condense and spray dry the extract, the product is the aqueous soluble extract powder of *Radix Glycyrrhizae*.

Preparation of evening primrose oil: commonly known as evening primroses, they are a series of flowering plants in the genus of *Oenothera*, the type genus of the family Onagraceae. Evening primrose oil is the fatty oil from evening primrose seeds. Collect ripe fruits of evening primrose in July or August, dry in the sun, crush, hull, and collect the seeds, extract oil by carbon dioxide ($CO_2$) supercritical fluid extraction.

Preparation of sea buckthorn seed oil: extract oil by carbon dioxide ($CO_2$) supercritical fluid extraction.

Prepare extract powder of *Semen Cassiae*

Ethanol soluble extract powder of *Semen Cassiae:* 10~60 parts

Aqueous soluble extract powder of *Radix Glycyrrhizae:* 2-10 parts

Evening primrose oil: 10~30 parts

Sea buckthorn seed oil: 5~20 parts

Beeswax: 2~10 parts

Dissolve 1000 grams ethanol soluble extract powder of *Semen Cassiae* in 2000 grams 95% ethanol, add 100 grams beeswax, heat in a water bath at 75 degrees Celsius to obtain a liquid mixture of ethanol soluble extract powder of *Semen Cassiae*, ethanol and beeswax; co-heat the 100 grams beeswax and 1000 grams evening primrose oil until the beeswax melts, let the mixture cool down to 60 degrees Celsius, add the above-mentioned mixture of ethanol soluble extract powder of *Semen Cassiae*, ethanol and beeswax while continuously stirring; add 200 grams aqueous soluble extract powder of *Radix Glycyrrhizae*, continue stirring and cool the mixture on circulated water until the temperature is 50 degrees Celsius; add 500 grams sea buckthorn seed oil, continue stirring until the mixture is homogenous with good fluidity; press soft capsules by conventional method with temperature below 40 degrees Celsius; the product is *Semen Cassiae* soft capsule for lowering blood lipids and losing weight (500 milligram per capsule).

Embodiment 2

Prepare ethanol soluble extract powder of *Semen Cassiae*, aqueous soluble extract powder of *Radix Glycyrrhizae*, evening primrose oil, and sea buckthorn seed oil as mentioned above.

Dissolve 3500 grams ethanol soluble extract powder of *Semen Cassiae* in 7000 grams 95% ethanol, add 300 grams beeswax, heat in a water bath at 75 degrees Celsius to obtain a liquid mixture of ethanol soluble extract powder of *Semen Cassiae*, ethanol and beeswax; co-heat the 300 grams beeswax and 2000 grams evening primrose oil until the beeswax melts, let the mixture cool down to 60 degrees Celsius, add the above-mentioned mixture of ethanol soluble extract powder of *Semen Cassiae*, ethanol and beeswax while continuously stirring; add 600 grams aqueous soluble extract powder of *Radix Glycyrrhizae*, continue stirring and cool the mixture on circulated water until the temperature is 50 degrees Celsius; add 1250 grams sea buckthorn seed oil, continue stirring until the mixture is homogenous with good fluidity; press soft capsules by conventional method with temperature below 40 degrees Celsius; the product is *Semen Cassiae* soft capsule for lowering blood lipids and losing weight (500 milligram per capsule).

Embodiment 3

Prepare ethanol soluble extract powder of *Semen Cassiae*, aqueous soluble extract powder of *Radix Glycyrrhizae*, evening primrose oil, and sea buckthorn seed oil as mentioned above.

Dissolve 6000 grams ethanol soluble extract powder of *Semen Cassiae* in 12000 grams 95% ethanol, add 500 grams beeswax, heat in a water bath at 75 degrees Celsius to obtain a liquid mixture of ethanol soluble extract powder of *Semen Cassiae*, ethanol and beeswax; co-heat the 500 grams beeswax and 3000 grams evening primrose oil until the beeswax melts, let the mixture cool down to 60 degrees Celsius, add the above-mentioned mixture of ethanol soluble extract powder of *Semen Cassiae*, ethanol and beeswax while continuously stirring; add 1000 grams aqueous soluble extract powder of *Radix Glycyrrhizae*, continue stirring and cool the mixture on circulated water until the temperature is 50 degrees Celsius; add 2000 grams sea buckthorn seed oil, continue stirring until the mixture is homogenous with good fluidity; press soft capsules by conventional method with temperature below 40 degrees Celsius; the product is *Semen Cassiae* soft capsule for lowering blood lipids and losing weight (500 milligram per capsule).

The present invention speeds up the metabolism of cholesterol and fat, and improves the hepatic metabolism; thus lowers the blood lipids and loses weight. Administration for 2 months with a daily dosage of 4-6 capsules (500 milligram per capsule) will see significant effects in patients.

The efficacy of the present invention has been tested in the following trial:

Select 100 patients with total cholesterol (TC) value greater than 7.76 m mol/l, low-density lipoprotein (LDL) value greater than 4.80 mmol/l, and body weight 20% greater than the standard value [Calculation of standard body weight: male standard body weight=(Height in centimeter−80 centimeters)×70%; female standard body weight=(Height in centimeter−70 centimeters)×60%], divide them into age groups shown in Table 1.

TABLE 1

| | Age Groups | | | | Sex | |
|---|---|---|---|---|---|---|
| | 30~40 | 41~50 | 51~60 | 61~70 | Male | Female |
| Number of People | 10 | 42 | 36 | 12 | 59 | 41 |

Patients are oral administrated of the *Semen Cassiae* soft capsules prepared in embodiment 2; 4 capsules daily for 4 months. All other medications are suspended during the trial. The result is shown in Table 2.

TABLE 2

| Recovered* | | Effective** | | Ineffective*** | | Total |
|---|---|---|---|---|---|---|
| Number of People | Ratio | Number of People | Ratio | Number of People | Ratio | Effective Ratio |
| 85 | 85% | 5 | 5% | 10 | 10% | 90% |

*Recovered: total cholesterol (TC) is 2.9-6.00 mmol/l, low-density lipoprotein (LDL) is 2.7-3.36 mmol/l, and body weight is standard weight ±5%
**Effective: total cholesterol (TC) is 6.00-7.00 mmol/l, low-density lipoprotein (LDL) is 3.36-4.00 mmol/l, and body weight is standard weight ±15%
***Ineffective: no changes in the measures.

Clinical observation shows the efficient rate of the present invention is 90%. Blood routine examination, urinalysis, liver and kidney function test before and after treatment show no abnormal change or adverse reaction.

TYPICAL CLINICAL EXAMPLES

Example 1

Male patient, 65 years old, body weight 76 kg, clinical examination shows total cholesterol (TC) value is 7.76 mmol/l, low-density lipoprotein (LDL) value is 4.80 mmol/l. Oral administrated *Semen Cassiae* soft capsules described in embodiment 1, 4 capsules daily for a period of 4 months, re-examination shows total cholesterol (TC) value is down to 6.07 mmol/l, low-density lipoprotein (LDL) value is down to 3.70 mmol/l, body weight is down to 68 kg.

Example 2

Female patient, 50 years old, body weight 65 kg, clinical examination shows total cholesterol (TC) value is 7.98 mmol/l, low-density lipoprotein (LDL) value is 5.02 mmol/l. Oral administrated *Semen Cassiae* soft capsules described in embodiment 3, 4 capsules daily for a period of 4 months, re-examination shows total cholesterol (TC) value is down to 6.02 mmol/l, low-density lipoprotein (LDL) value is down to 3.51 mmol/l, body weight is down to 61.5 kg.

What is claimed is:

1. A soft capsule for lowering blood lipids and reducing weight in a subject in need thereof, the soft capsule consisting of the following components, by weight part:
    ethanol-soluble extract powder of *Semen Cassiae*, 10-60 parts;
    aqueous-soluble extract powder of *Radix Glycyrrhizae*, 2-10 parts;
    evening primrose oil, 10-30 parts;
    sea buckhorn seed oil, 5-20 parts; and
    beeswax, 2-10 parts.

2. A method for making the soft capsule of claim 1 comprising the following steps:
    (1) (a) preparing the ethanol-soluble extract powder of *Semen Cassiae* by grinding *Semen Cassiae* into a powder;
        forming an ethanol extract by reflux-extracting the powder in 95% ethanol at a level of 10-20 times the weight of the powder;
        vacuum-distilling then spray-drying the extract;
    (b) preparing the aqueous-soluble extract powder of *Radix Glycyrrhizae* by grinding *Radix Glycyrrhizae* into a powder;
        forming an aqueous extract by adding boiling water to the powder at a level of 10-20 times the weight of the powder;
        condensing then spray-drying the extract;
    (2) dissolving the ethanol-soluble extract powder of *Semen Cassiae* (a) in two times the weight of 95% ethanol;
        adding half of the beeswax to the ethanol-dissolved extract powder to form a first mixture;
        heating the first mixture in a water bath at 75° C.;
        adding the other half of the beeswax to the evening primrose oil to form a second mixture;
        adding the first mixture to the second mixture while continuously stifling to form a third mixture;
        adding the aqueous-soluble extract powder of *Radix Glycyrrhizae* (b) to the third mixture to form a fourth mixture;
        cooling the fourth mixture in a circulating water bath;
        adding the sea buckthorn seed oil to the cooled fourth mixture to form a fifth mixture; and
        encapsulating the fifth mixture in a soft capsule.

* * * * *